United States Patent
Ritchie et al.

(10) Patent No.: US 9,931,482 B2
(45) Date of Patent: Apr. 3, 2018

(54) NECK SEAL FOR A GAS TREATMENT HOOD

(71) Applicant: Amron International, Inc., Vista, CA (US)

(72) Inventors: Scott Craig Ritchie, Valley Center, CA (US); Christopher Eames Woolley, San Marcos, CA (US)

(73) Assignee: Amron International, Inc., Vista, CA (US)

( * ) Notice: Subject to any disclaimer, the term of this patent is extended or adjusted under 35 U.S.C. 154(b) by 385 days.

(21) Appl. No.: 14/681,935

(22) Filed: Apr. 8, 2015

(65) Prior Publication Data

US 2015/0290480 A1 Oct. 15, 2015

Related U.S. Application Data

(60) Provisional application No. 61/977,859, filed on Apr. 10, 2014.

(51) Int. Cl.
| | |
|---|---|
| *A61M 16/06* | (2006.01) |
| *A62B 17/04* | (2006.01) |
| *A61M 16/00* | (2006.01) |
| *A62B 17/00* | (2006.01) |
| *A41D 13/00* | (2006.01) |

(52) U.S. Cl.
CPC ......... *A61M 16/00* (2013.01); *A41D 13/0005* (2013.01); *A61M 16/06* (2013.01); *A61M 16/0627* (2014.02); *A62B 17/04* (2013.01); *A41D 2300/30* (2013.01)

(58) Field of Classification Search
CPC ....... A61G 10/04; A61M 16/00; A61M 16/06; A61M 16/0627; A61M 16/107; A61M 16/20; A61M 16/208; A61M 16/22; A61M 2016/0027; A61M 2016/003; A61M 2202/0208; A61M 2205/3331; A61M 2205/7545; A62B 17/04; A62B 25/00; A62B 7/08; A62B 9/02
USPC ............ 128/200.28, 201.22, 201.23, 201.24, 128/201.25, 201.29, 205.26, 206.24; 2/171.3, 205, 413, 421, 424, 6.2
See application file for complete search history.

(56) References Cited

U.S. PATENT DOCUMENTS 3,740,764 A * 6/1973 Elfstrom ................. B63C 11/08
  2/2.16
4,015,295 A * 4/1977 Lancaster ............... B63C 11/06
  2/2.15

(Continued)

FOREIGN PATENT DOCUMENTS

FR 2477892 A1 * 9/1981 ............. B63C 11/06

*Primary Examiner* — Annette Dixon
(74) *Attorney, Agent, or Firm* — Knobbe Martens Olson & Bear LLP

(57) ABSTRACT

A seal for a gas treatment hood assembly is disclosed. The hood assembly is placeable over a user's head for treating a user with a gas such as oxygen. The assembly may have a neck ring around a user's neck with an elastomeric, tubular neck seal with one end of the neck seal connected to the neck ring and the other end configured to fit around the user's neck. The neck seal may have a double sealing element construction and may also have variable thickness along a sidewall for enhanced structural properties and improved patient comfort. The seal and hood assembly may be used in providing oxygen to a patient in a hyperbaric chamber.

20 Claims, 8 Drawing Sheets

(56) References Cited

U.S. PATENT DOCUMENTS

| | | | |
|---|---|---|---|
| 4,484,575 A | 11/1984 | Brockway et al. | |
| 4,683,880 A | 8/1987 | Werjefelt | |
| 5,133,344 A | 7/1992 | Jurrius et al. | |
| 5,226,409 A | 7/1993 | Bower et al. | |
| 5,653,225 A * | 8/1997 | Schegerin | A62B 17/04 128/201.22 |
| 5,819,728 A * | 10/1998 | Ritchie | A62B 17/04 128/201.22 |
| 6,701,920 B1 * | 3/2004 | Cox | A62B 17/04 128/201.22 |
| 6,854,459 B1 * | 2/2005 | Cox | A62B 17/04 128/201.22 |
| 7,743,433 B1 * | 6/2010 | Grove | A62B 17/00 2/465 |

\* cited by examiner

NECK SEAL FOR A GAS TREATMENT HOOD

CROSS-REFERENCE TO RELATED APPLICATIONS

This application claims the benefit of U.S. Provisional Patent Application No. 61/977,859, filed Apr. 10, 2014, entitled NECK SEAL FOR A GAS TREATMENT HOOD, the disclosure of which is incorporated herein by reference in its entirety.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

This disclosure relates generally to seals. In particular, features for providing a seal in a hood covering a user's head are disclosed.

Description of the Related Art

A wide variety of hoods have been developed for enclosing the head of a user and directing oxygen, clean air or other gases into the hood. Generally the hood is at least partially transparent so that the wearer can see out of the hood and a seal is provided around the wearer's neck to prevent the gas being introduced into the hood from leaking out and/or preventing outside gases from entering the hood. These prior hoods vary greatly in effectiveness and wearer comfort.

Some hoods, such as those described by Bower et al. in U.S. Pat. No. 5,226,409 and Werjefelt in U.S. Pat. No. 4,683,880 are intended for protection from toxic gases in the event of a fire or the like. The hood includes a tubular body, a circular top and an elastic lower panel having a circular opening for slipping over a user's head and sealing against the neck. An inlet for clean air is provided in the top or side of the hood. While effective for short time use in a toxic gas environment, the narrow neck seal and sealing pressure against the neck is uncomfortable and abrading if used for extended periods. Also, having the inlet at the top or side will tend to pull the hood to the side, possibly disrupting the seal and causing the hood to distort and press against the user's head.

Other hoods of the sort described by Jurris et al. in U.S. Pat. No. 5,133,344 and Brockway et al. in U.S. Pat. No. 4,484,575 have panels that extend down over the user's body, perhaps tucked under a smock, to avoid the neck seal problem. However, without an effective seal the gas being directed into the hood can easily leak out, which is undesirable where the gas is oxygen, an anesthetic gas or other special gas.

Where the gas being introduced into the hood is part of hyperbaric oxygen therapy, it is important that all exhaust gas be collected and piped away, since otherwise the oxygen content in the treatment chamber and/or treatment room will increase, resulting in high risk of fire.

Generally, hyperbaric oxygen therapy is conducted on an intermittent basis with pure oxygen or with gases containing high percentages of oxygen in a hyperbaric chamber maintained at increased barometric pressure. At these high chamber pressures a patient can tolerate higher doses of oxygen for longer periods than otherwise attainable. Also, this results in a large increase in the partial pressure of oxygen dissolved in the blood. In addition to the oxygen transported by the hemoglobin, the oxygen carried in a dissolved state is greatly increased.

Hyperbaric oxygen therapy has been used in treatment of a number of different conditions, such as treatment of decompression sickness, arterial or venous gas embolism, gas gangrene, carbon monoxide poisoning, and as an aid to the healing of slow or non-healing wounds.

While in some cases a face mask is useful in administering oxygen to a patient in a hyperbaric chamber, the masks are uncomfortable for extended use, may leak oxygen into the chamber and cannot be used with patients with facial injuries, facial medical appliances, etc.

Treatment with oxygen in a hyperbaric chamber may require daily treatment for extended periods. It is important that the treatment apparatus be comfortable and non-injurious. Where a tight elastic neck seal, or a seal having an edge taped to the patient's body is used, considerable discomfort, abrasion and tape burns may result from extended treatment.

A treatment hood must sit lightly and be well balanced on the patient's body, since a heavy or off-center weight will tend to cause pain in the neck or shoulder muscles with extended use. The hood should be capable of being easily put on and removed by the user or an assistant and comfortable for the user when the user is in a reclining position.

Therefore, there is a continued need for improved hoods for administering selected gases, such as oxygen in hyperbaric oxygen treatment programs, that are comfortable in use and can be used by the user in a reclining position, that prevent leakage of the treatment gas into the atmosphere, that have seals that will not significantly damage or irritate the user's skin, that are light in weight and well balanced and can be easily put on or taken off by the user with little, if any, assistance.

Further, conventional neck seal technology uses a ring that is separate from the neck seal, such as an O-ring, which is a separate component that is assembled with the neck seal as part of the hood assembly process. However, a separate ring may be lost or damaged prior to its engagement with the neck seal and integration with the overall hood assembly. A separate sealing ring also creates complexity as the neck seal and the separate sealing part, such as a separate O-ring seal, must be separately managed and then assembled into the hood assembly.

Neck seals with rolled latex seals are typically implemented, but the neck seals are used often in medical settings, such as hospitals, where patients may have allergic reactions to latex. As an alternative to latex, neoprene may be used instead. However, neoprene rips and tears easily. Further, neoprene also has unfavorable material properties such as low stretch, low tear resistance, poor memory retention, and will permanently deform from its original shape, thus making thickening of the neoprene an impractical solution as this doesn't allow the neck seal to easily stretch over a patient's head.

There is therefore a further need for improved neck seal technology that overcomes these drawbacks.

SUMMARY

The hood assembly of this disclosure may comprise a neck ring for encircling a user's neck, a tubular and resilient or elastic neck seal that releasably secures the neck ring at a first end and is configured to fit around a user's neck at the other, and an at least partially transparent hood secured to a hood ring, with the hood ring fastenable to the neck ring in a sealing relationship. The centerline through the neck seal may be off-set from the center line through the neck ring.

The neck seal may further incorporate various features for providing a comfortable, simple and durable seal. In some embodiments, the neck seal has one or more sealing elements such as rectangular or square projections that seal the interface with the neck ring. For example, the neck seal may have two inward, rectangular projections near the base that couple with a complementary structure of the hood assembly. In some embodiments, the neck seal has variable thicknesses along a sidewall to provide a robust yet comfortable seal. For example, the neck seal may have a decreasing thickness from the base of the seal to the top of the seal. In some embodiments, the neck seal sidewall has a straight section of uniform thickness, followed by a curved section of decreasing thickness, followed by another straight section of uniform but smaller thickness. Further, an injection molding process may be used to create the neck seal having variable thicknesses and/or multiple sealing elements of various cross-sectional shapes.

In a first aspect, several embodiments for a neck seal for a gas treatment hood are disclosed. In some embodiments, the neck seal comprises a tubular stretchable base configured to seal with a tubular neck ring, and a tubular stretchable upper comprising a sidewall extending upward from the base to a top of the upper, with the top forming an opening configured to fit around a user's neck. In some embodiments, a first thickness of the sidewall adjacent to the base is greater than a second thickness of the sidewall adjacent to the top.

In some embodiments, the sidewall further comprises a plurality of intermediate thicknesses that decrease substantially uniformly along at least a portion of the sidewall from the first thickness to the second thickness.

In some embodiments, the sidewall further comprises a first substantially straight section coupled with the base and having a first straight section thickness equal to the first thickness, a curved section having a lower end and an upper end, wherein the lower end is coupled with the first straight section, and a second substantially straight section coupled with the upper end of the curved section and having a second straight section thickness equal to the second thickness. In some embodiments, the curved section comprises a plurality of intermediate thicknesses that decrease substantially uniformly, from a first curved section thickness at the lower end that is equal to the second thickness, to a second curved section thickness at the upper end that is equal to the second thickness.

In some embodiments, the first thickness adjacent to the base is between approximately 0.015 inches and 0.100 inches inclusive, and the second thickness adjacent to the top is between approximately 0.010 inches and 0.050 inches inclusive. In some embodiments, the first thickness adjacent to the base is about 0.060 inches and the second thickness adjacent to the top is about 0.040 inches.

In some embodiments, the first thickness is about 25% to 300% thicker than the second thickness. In some embodiments, the first thickness is about 50% thicker than the second thickness.

In some embodiments, the neck seal comprises a material with a Shore Hardness A Durometer between approximately 10 and 30, inclusive. In some embodiments, the neck seal comprises a material with a Shore Hardness A Durometer between approximately 20 and 25, inclusive. In some embodiments, the neck seal is silicone. In some embodiments, the silicone is medical grade Class VI silicone.

In some embodiments, the neck seal with variable thicknesses is included in a gas treatment hood assembly, along with a hood and a neck ring.

In some embodiments, the base further comprises at least two sealing elements configured to couple with the tubular neck ring.

In another aspect, a neck seal for a gas treatment hood is disclosed where the neck seal comprises a tubular stretchable upper comprising a top with an opening configured to fit around a user's neck, a tubular stretchable base coupled with the upper, which may be at a lower portion or region of the upper, wherein the upper extends upwardly from the base, and at least first and second sealing elements coupled with the base and configured to seal with a tubular neck ring.

In some embodiments, at least one of the first and second sealing elements has a substantially rectangular cross-section. In some embodiments, at least one of the first and second sealing elements has a substantially non-circular cross-section. In some embodiments, at least one of the first and second sealing elements comprises a substantially straight side with a substantially flat surface.

In some embodiments, the first and second sealing elements each comprise a tubular top surface, a tubular inner surface and a tubular bottom surface, wherein, when coupled with the tubular neck ring, the top and bottom surfaces are substantially horizontal and the inner surfaces are substantially vertical.

In some embodiments, the first and second sealing elements are longitudinally spaced with respect to each other. In some embodiments, the first and second sealing elements each comprise a protrusion extending inwardly from the base. In some embodiments, the base and the first and second sealing elements comprise a unitary, molded construction.

In some embodiments, the base and the first and second sealing elements comprise the same material. In some embodiments, the neck seal has a Shore Hardness A Durometer between approximately 10 and 30, inclusive. In some embodiments, the neck seal has a Shore Hardness A Durometer between approximately 20 and 25, inclusive. In some embodiments, the neck seal is silicone. In some embodiments, the silicone is medical grade Class VI silicone.

In some embodiments, a gas treatment hood assembly is disclosed comprising the neck seal with two sealing elements, a hood and a neck ring.

In some embodiments, the tubular elastomeric upper further comprises a sidewall extending upward from the base to the top, with a first thickness of the sidewall adjacent to the base that is greater than a second thickness of the sidewall adjacent to the top. In some embodiments, the sidewall further comprises a plurality of intermediate thicknesses that decrease substantially uniformly along the sidewall from the first thickness to the second thickness. In some embodiments, the upper further comprises a first substantially straight section coupled with the base and having a first straight section thickness equal to the first thickness, a curved section having a lower end and an upper end with the lower end coupled with the first straight section, and a second substantially straight section coupled with the upper end of the curved section and having a second straight section thickness equal to the second thickness. In some embodiments, the curved section comprises a plurality of intermediate thicknesses that decrease substantially uniformly, from a first curved section thickness at the lower end equal to the second thickness, to a second curved section thickness at the upper end equal to the second thickness.

In some embodiments, the sidewall further comprises a plurality of intermediate thicknesses that decrease substantially uniformly along the sidewall from the first thickness to the second thickness and the first thickness adjacent to the base is about 0.060 inches and the second thickness adjacent to the top is about 0.040 inches.

In another aspect, a neck ring for a gas treatment hood is disclosed, wherein the neck ring includes a tubular base, a sidewall and at least two protrusions. The tubular base forms an opening configured to fit around a user's neck. The sidewall extends from the base. The at least two protrusions extend from the base. The two protrusions form at least two annular grooves in the base. The annular grooves each are configured to receive a corresponding sealing element of a tubular neck ring.

In some embodiments, the sidewall extends radially outwardly from the base.

In some embodiments, the at least two protrusions extend radially outwardly from the base.

In some embodiments, the at least two protrusions are longitudinally spaced with respect to each other.

In some embodiments, the at least two annular grooves comprise a first annular groove formed between a first of the at least two protrusions and a second of the at least two protrusions, and a second annular groove formed between a second of the at least two protrusions and the sidewall.

In some embodiments, the sidewall extends approximately orthogonally from the base.

In some embodiments, the protrusions extend approximately orthogonally from the base.

In some embodiments, at least one of the at least two annular grooves has a substantially rectangular cross-section.

In some embodiments, at least one of the at least two annular grooves has a substantially non-circular cross-section.

In some embodiments, at least one of the at least two annular grooves comprises a substantially straight side with a substantially flat surface.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the "detailed description" section, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure. Details of the invention, and of preferred embodiments thereof, will be further understood upon reference to the drawings, wherein:

DETAILED DESCRIPTION

The following detailed description is directed to certain specific embodiments of the development as described with reference to FIGS. 1-5C. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Described herein are neck seals for engaging around a user's neck and a neck ring for a gas treatment hood assembly. The neck seals can include various geometric configurations to provide improved sealing and comfort around the user's neck and/or the neck ring. For example, some implementations include at least two sealing elements to engage (e.g. seal) with the neck ring. These sealing elements can be configured, not only to provide additional sealing, but to improve mechanical engagement with the neck ring, with respect to previous single seal designs. For example, a neck seal with a single sealing element will roll off the neck ring, whereas a neck ring with at least two sealing elements can provide lateral and longitudinal stability to prevent such disengagement of the neck seal from the neck ring. Sealing elements with specific geometric structure that further improve upon these advantages are also provided.

Some implementations provide a neck seal with a greater thickness at its lower (base) opening relative to its upper (neck) opening. Such relative dimensioning between select portions of the neck seal can provide improved comfort at the user's neck, with increased strength (and thus improved sealing) at its base, which seals with the neck ring. Neck seals that include specific materials selected to further improve the aforementioned advantages are also provided.

Figure 1:
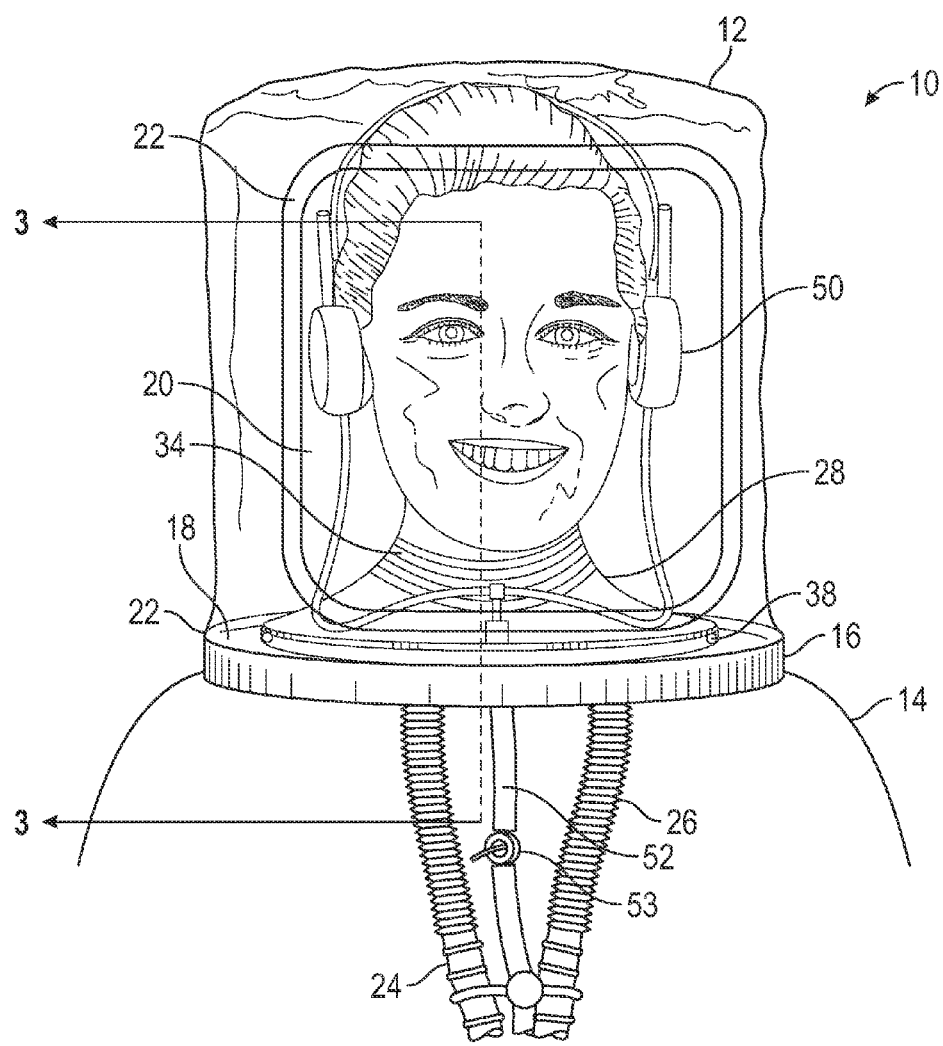
FIG. 1 is a front elevation view of an embodiment of a hood assembly having a neck seal.

As seen in FIG. 1, the gas treatment hood assembly 10 may include a hood 12 that surrounds the head of the user 14 and an assembly of a hood ring 16 and a neck ring 18 that encircles the neck of user 14.

The hood 12 may be at least partially transparent or translucent, with at least the viewing window 20 immediately in front of the eyes of the user 14 being transparent and of optical quality. For flexibility in use and storage and good visibility from within the hood 12, a viewing window may be formed from a shape retaining transparent plastic sheet material, typically an optical quality press finished vinyl, acrylic, polycarbonate or other suitable plastic. The viewing window may have a thickness, for example, of from about 0.024 to 0.059 inches (0.600 to 1.50 mm). The viewing window 20 may be semi-rigid with some flexibility and have high strength and impact resistance.

The hood 12 may be formed from a transparent or translucent, flexible, soft but strong plastic sheet, typically a vinyl or other suitable plastic, having a thickness, for example, of from about 0.005 to 0.021 inches (0.125 to 0.550 mm). The viewing window 20 may be bonded to the hood 12 along an interface 22 in any suitable manner, such as heat or adhesive bonding.

As detailed below, a gas inlet tube 24 and a gas outlet tube 26 may be connected to ports 46 (see FIG. 2) in the neck ring 18 to admit a selected gas, such as oxygen, into the hood 12 and to evacuate a mixture of the gas and carbon dioxide produced by respiration from the hood 12. Any suitable gas may be introduced into the hood. An example use of the hood assembly is in treatment with pure oxygen or high oxygen concentration gases in a hyperbaric chamber. However, other gases could be used such as air including an anesthetic gas, air with added gases for the treatment of emphysema or other diseases, etc.

The flexibility of the hood 12 can be sufficient such that the viewing window 20 can be folded back against the hood ring 16 when not in use. The hood 12 can be bonded over the inner or outer circumference of the hood ring 16 in any suitable manner, such as by an adhesive, heat sealing, etc.

Figure 2:
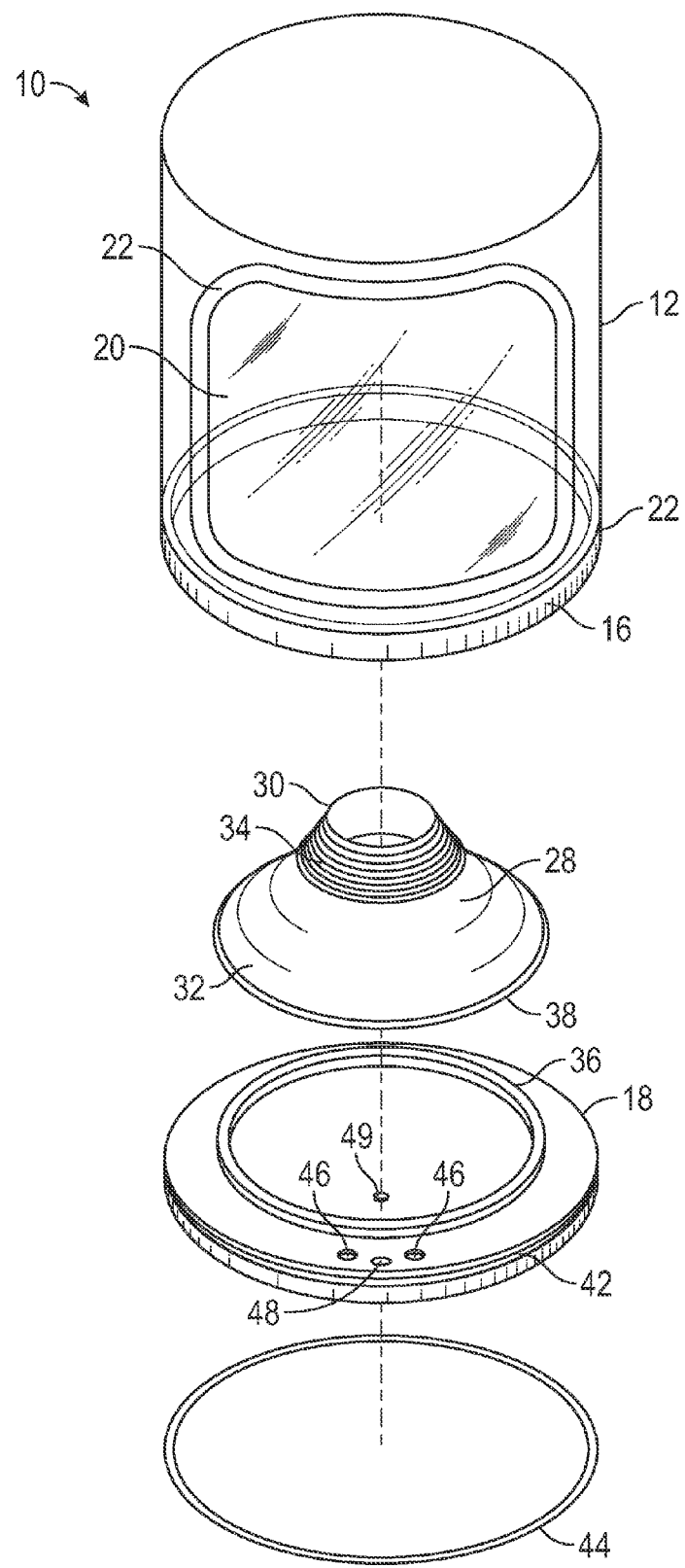
FIG. 2 is an exploded view of the hood assembly of FIG. 1 showing embodiments of various components of the assembly.
Figure 3:
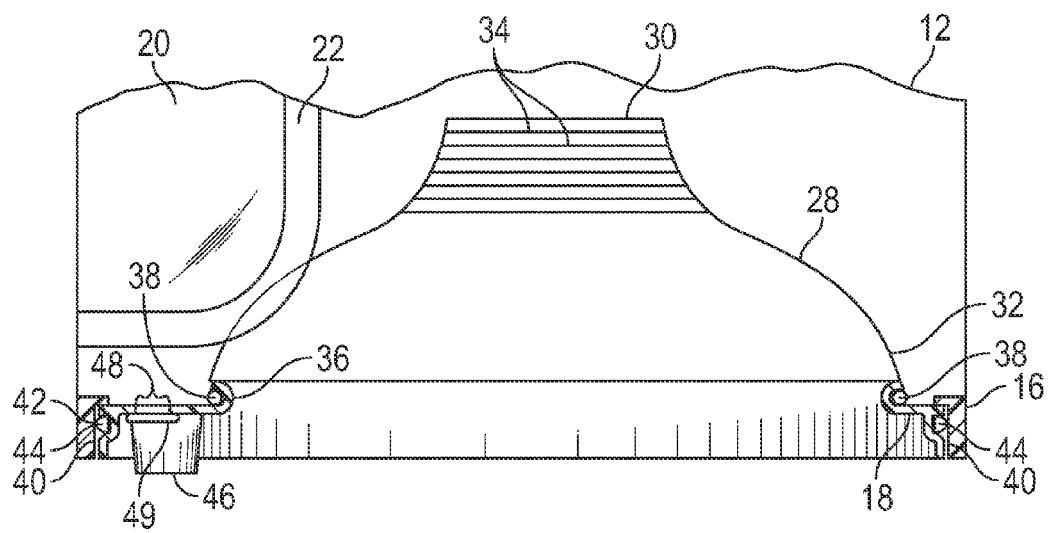
FIG. 3 is an axial section view through the hood assembly, taken along line 3-3 in FIG. 1.

As best seen in FIGS. 2 and 3, the neck seal 28 has a generally tubular shape, with a proximal end 32 with an opening forming a perimeter (e.g., circumference) that is typically larger than a corresponding opening formed by a perimeter of a distal end 30. Distal end 30 can be a generally frustoconical shape. "Tubular" here refers to any generally elongated structure with a sidewall of any suitable cross-sectional shape forming a closed perimeter and inner lumen, and need not be perfectly round, as is discussed in further detail herein, for example with respect to FIGS. 4A-4E. The neck seal 28 may be formed from any soft, resilient sheet material such as silicone, latex, elastic polymer or the like, as is discussed in further detail herein, for example with respect to FIGS. 4A-4E.

Indicia 34 may be provided along the distal end 30 of the neck seal 28 to aid in trimming that end to provide a comfortable sealing fit along the user's neck. The indicia 34 may comprise a series of spaced circumferential lines and numbers indicating standard neck sizes. A user's neck size can be easily determined by measuring the neck circumference.

The distal end 30 can be simply trimmed with scissors or the like along a selected line. This provides a particularly comfortable sealing fit, which is of considerable importance in preventing skin abrasion or "tape burns" where the hood is used for relatively long periods.

As seen in FIG. 1, the neck seal 28 may extend upwardly along the neck skin so that pressure within the hood 12 will aid in pressing the ring lightly against the skin to assure a positive seal without excess elastic pressure of the neck seal 28 material against the neck.

The neck seal 28 may be releasably secured to the neck ring 18 for easy removal for cleaning or replacement to accommodate different users of the hood assembly 10. The neck ring 18 may have a peripheral outwardly extending recess 36 (see FIGS. 2 and 3). The proximal end 32 of the neck seal 28 may be fitted over the recess 36 and stretched and snapped into the recess 36. In some embodiments, a seal like elastic ring 38 may be molded into the neck seal 28. The neck seal 28 may have other features that provide a sealing and attachment capability, as is discussed in further detail herein, for example with respect to FIGS. 4A to 4E.

A periphery 40 of the neck ring 18 may have a circumferential, inwardly extending groove 42 in which an elastic sealing ring 44, such as an O-ring, is inserted with the sealing ring 44 extending outwardly slightly above the periphery 40. When the neck ring 18 is pressed into the hood ring 16, as seen in FIG. 2, the sealing ring 44 may both seal against gas leakage from within the hood assembly 10 and hold the neck ring 18 and hood ring 16 together. The groove 42 could be formed in either mating surface, the outer surface of neck ring 18 or inner surface of hood ring 16, as desired. If the groove 42 is used in the inner surface of the hood ring 16, the circumference of the ring 44 may be equal to or slightly greater than the groove circumference to hold the ring 44 in place.

Generally, the neck ring 18 and the neck seal 28 are placed over the user's head, an audio headset or other devices are installed, the hood 12 and the hood ring 16 are placed over the user's head, and the hood 12 and neck rings 18 and 16, respectively, are brought together.

One or more ports 46 may be provided through the neck ring 18 to receive ends of inlet and outlet tubes 24 and 26, respectively (see FIG. 1). The center line of the opening at the distal end 30 of the neck seal 28 may be offset from the center line of the hood ring 16 rearwardly from the viewing window, which allows the user to sit or recline without the user's face touching the viewing window and allows the ports 46 to be positioned in the front of the hood 12 adjacent to the viewing window. The ports 46 may be located in the neck ring 18 at a location adjacent to the user's face spaced forwardly therefrom, so that incoming gas will pass along the user's face and viewing window 20, clearing any mist deposits on the viewing window and cooling the user's face and reducing exterior noise. Having the ports 46 in the neck ring 18 rather than through the top or sides of the hood 12 is advantageous in not pulling the hood down on the user's head and in allowing the user to recline without his or her head encountering or disturbing the gas supply and evacuation hoses. In addition, the position of the ports, as shown and described above, allows the inlet gas to flow over the user's head, down the user's back, towards the front viewing window, flushing excess gas out of the exhaust port along with the user's exhaled breath. This feature provides improved gas transfer with minimal $CO_2$ build-up.

At least one additional port 48 may be provided between or near the port 46 for insertion of a conventional gas composition measuring device, pneumatic audio headset 50 or the like. FIG. 1 shows pneumatic audio tubes 52 with a series volume control valve 53 passing through port 48 to headset 50. Pneumatic tubes for conveying sound to headset 50 are preferred over conventional electromagnetic headsets, since it is important to keep any electrical devices away from the often high oxygen content of hood 12. When not in use, the port 48 may be closed by a plug 49.

Figure 4A:
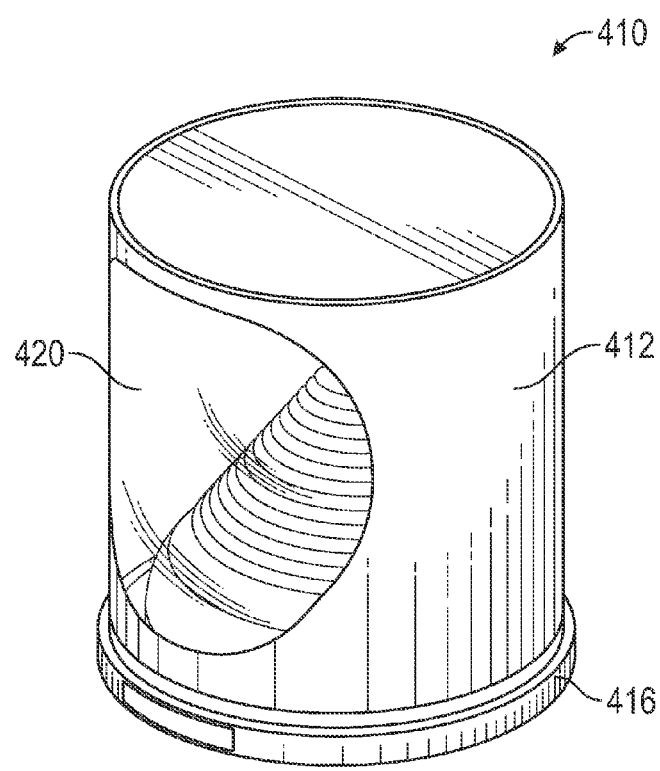
FIG. 4A is a perspective view of an embodiment of a hood assembly with an embodiment of a neck seal having a double projection seal.
Figure 4B:
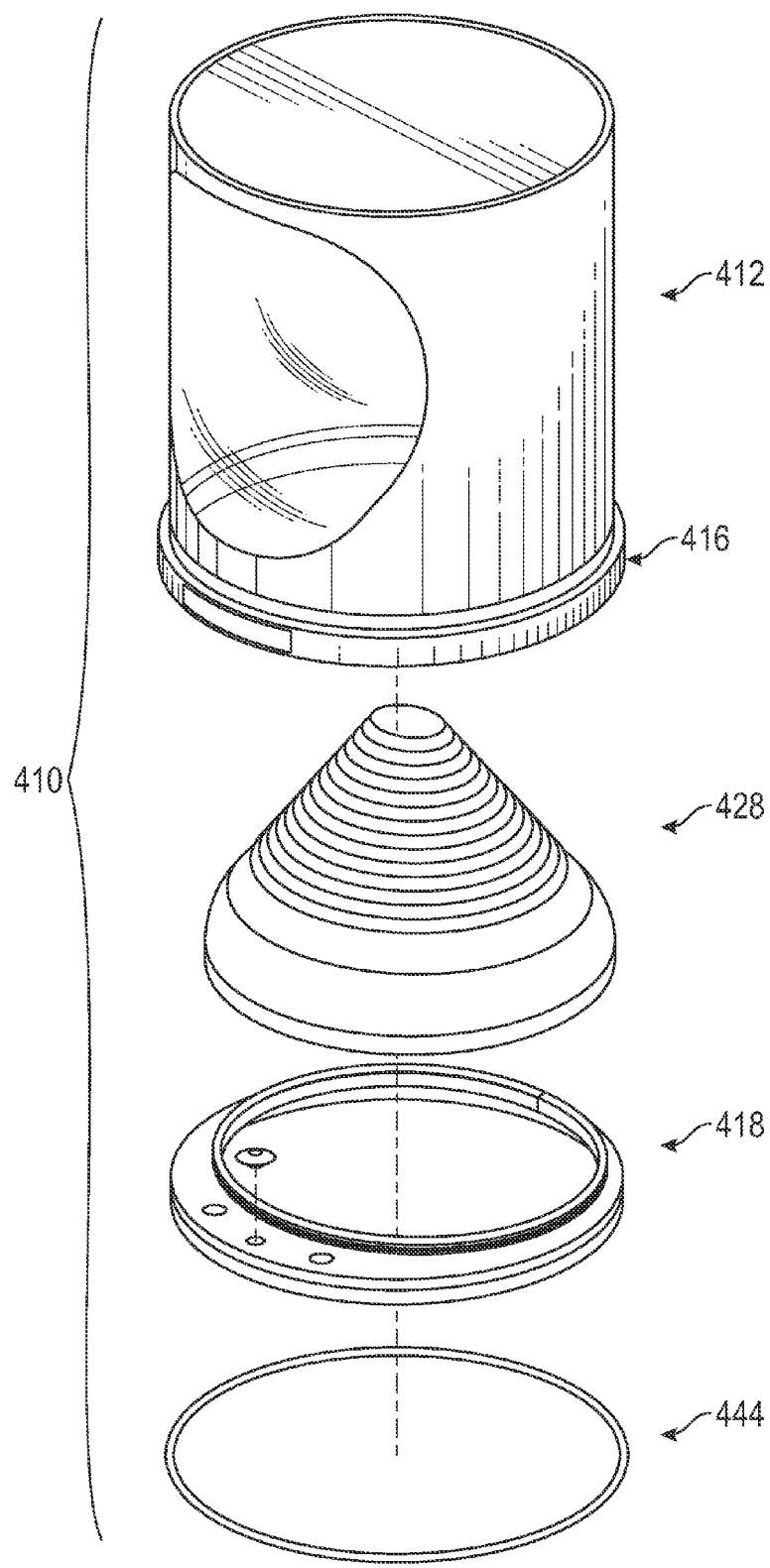
FIG. 4B is an exploded view of the hood assembly of FIG. 4A.
Figure 4D:
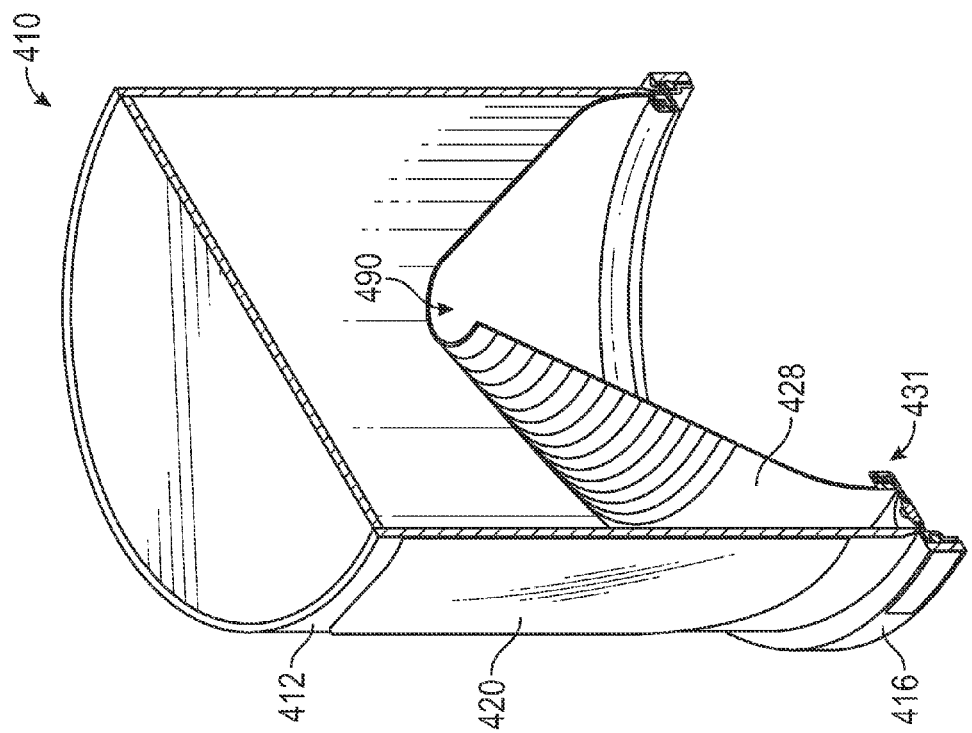
FIGS. 4C and 4D are cross-section views of the hood assembly of FIG. 4A.
Figure 4C:
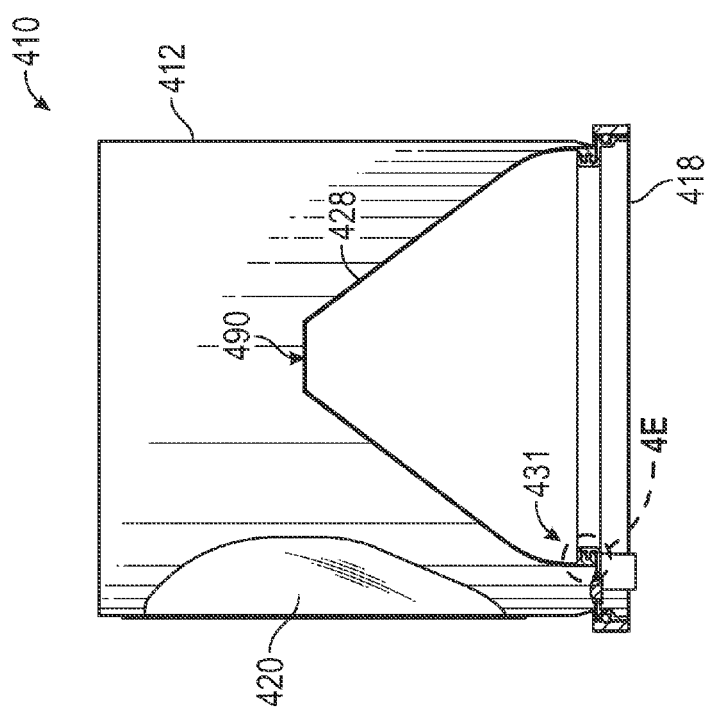
Figure 4E:
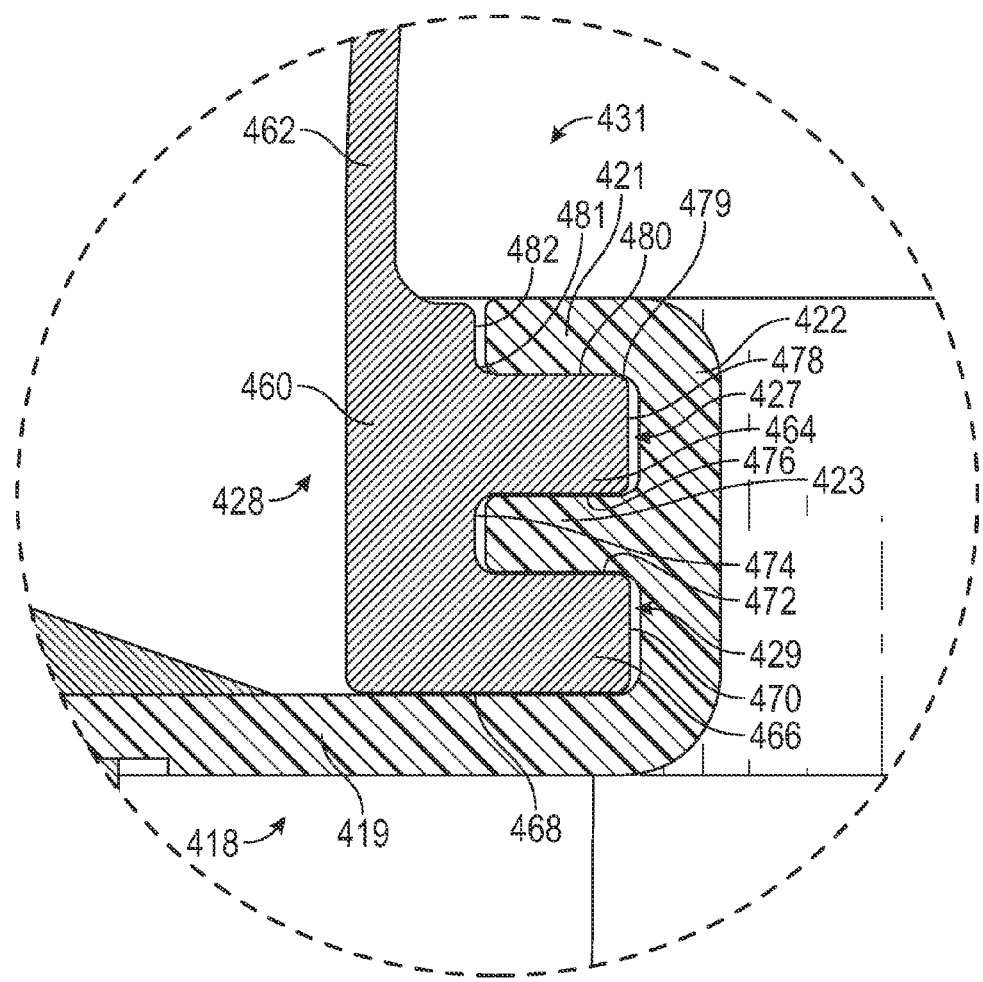
FIG. 4E is a detail view of the double projection seal mated with a neck ring, taken from detail 4E as indicated in FIG. 4C.

FIGS. 4A-4E are various views of an embodiment of a hood assembly 410. The hood assembly 410 may have the same or similar features as other hood assemblies described herein, for example the hood assembly 10, and vice versa. The hood assembly 410 may have a neck seal 428 that includes a double projection seal. FIG. 4A is a perspective view of the hood assembly 410. FIG. 4B is an exploded view of the hood assembly 410. FIGS. 4C and 4D are cross-section views of the hood assembly 410. FIG. 4E is a detail view, taken from FIG. 4C, of an embodiment of a double projection seal mated with a neck ring 416.

Referring to FIGS. 4A and 4B, the hood assembly 410 may include a hood 412. The hood 412 may have the same or similar features as other hoods described herein, for example the hood 12, and vice versa. As shown, the hood 412 may include a viewing window 420. The viewing window 420 may have the same or similar features as other viewing windows described herein, for example the viewing window 20, and vice versa. The hood assembly 410 may include a neck seal 428. The neck seal 428 may have the same or similar features as other neck seals described herein, for example the neck seal 28, and vice versa. The hood assembly 410 may include a hood ring 416. The hood ring 416 may have the same or similar features as other hood rings described herein, for example the hood ring 16, and vice versa. The hood assembly 410 may include a neck ring 418. The neck ring 418 may have the same or similar features as other neck rings described herein, for example the neck ring 18, and vice versa. The hood assembly 410 may include an elastic sealing ring 444. The sealing ring 444 may have the same or similar features as other sealing rings described herein, for example the sealing ring 44, and vice versa.

FIGS. 4C and 4D are cross-section views of the hood assembly 410. FIG. 4C is a side cross-section view and FIG. 4D is a perspective cross-section view of the hood assembly 410. As shown in FIGS. 4C and 4D, the hood 412 and neck seal 428 are coupled to the neck ring 418. An interface between the hood 412 and the neck ring 418 is near the bottom of the hood 412, as oriented in FIGS. 4C and 4D. An interface 431 between the neck seal 428 and neck ring 418 is near the bottom of the neck seal 428, as oriented in FIGS. 4C and 4D. Cross-sections of these interfaces are visible. A location of the interface 431 between the neck seal 428 and the neck ring 418 is identified by circular detail 4E. A close up view of this detail is shown in FIG. 4E.

The neck seal 428 and parts thereon may be tubular. "Tubular" as used herein refers to a generally elongated structure with a sidewall forming a closed perimeter, and includes circular, elliptical, oval, and other suitable shapes. It may further include a closed perimeter that includes curvilinear sections and substantially straight sections. For instance, the neck seal 428 may be elliptical or non-circular with some straight segments before coupling with the neck ring 418, and then the neck seal 428 may take a generally circular shape when coupled with the neck ring 418. The term tubular covers the shape of the neck seal 428 in this instance both before and after coupling with the neck ring 418.

Further, while discussion of the neck seal 428 and associated parts may be in the context of a cross-section view of the neck seal 428 or those parts, it is understood that this is not meant to imply that the neck seal 428 or associated parts are limited to a circular shape. Any cross-sections discussed may therefore be in a circular embodiment, an elliptical embodiment, etc., all of which are covered by the term "tubular." Further, the particular cross-section discussed may be at any location or position within the neck seal 428 and is not limited to any particular position, unless otherwise noted.

As shown in FIGS. 4C and 4D, the neck seal 428 may form an opening 490 near the distal end (e.g., top) of the neck seal 428, as oriented in the figure. The opening 490 may be a space defined by the tubular neck seal 428. The opening 490 allows for a user to place their head through the neck seal 428. The edge of the neck seal 428 near the opening 490 would then be around the user's head or neck. As mentioned, the neck seal 428 may be trimmed to different sizes. Therefore, the opening 490 may be in a variety of longitudinal locations on the neck seal 428 and may be a variety of sizes and shapes. In some embodiments, the opening 490 is small and far from the neck ring 418, as oriented in the figure. In some embodiments, the opening 490 is larger and closer to the neck ring 418, as oriented in the figure. The opening 490 may further be tubular. In some embodiments, the opening 490 is circular, elliptical, oval, or otherwise round or partially round. The opening 490 may further be different shapes depending on whether the neck seal 428 is in a free state, is coupled with the neck ring 418, and/or is around a user's head and/or neck. "Free state" here refers to a quiescent or unbiased state, of the neck seal 428, for example, when not stretched around or engaged with the neck ring 418, a user's neck, or otherwise subject to external forces. In some embodiments, the opening 490 may be elliptical with straight segments in the free state, generally circular when coupled with the neck ring 418, and round but non-circular when placed around a user's neck.

FIG. 4E is a detail of a cross-section view of the interface 431 between embodiments of the neck seal 428 and the neck ring 418, taken from detail 4E in FIG. 4C. This interface serves a number of functions. Among them is the prevention or mitigation of the flow of gas across the interface. Gas flow across the interface may be prevented or mitigated by the neck seal 428 coupling with the neck ring 418. In some embodiments, the neck seal 428 elastically fits around the neck ring 418 such that the neck seal 428 provides a force against and thus seals with the neck ring 418. For the part of the cross-section of the neck seal 428 as shown and oriented in FIG. 4E, the neck seal 428 may exert an inward force, such as in a direction to the right. The elasticity of the neck seal 428 may provide this force, such that any gaps between the neck seal 428 and neck ring 418 at the interface are closed or substantially closed. Substantially here indicates a configuration such that gas flow across the interface is prevented or mitigated.

The cross-section view in FIG. 4E shows an embodiment of the neck seal 428 having a base 460 and an upper 462. The base 460 is generally stretchable and configured to seal with the neck ring 418, and the upper 462 is generally stretchable and configured to seal with a user's neck. In some embodiments, the base 460 and upper 462 are tubular. For instance, the base 460 and upper 462 may be a circular, elliptical, or other round shape formed in part from the cross-section view shown in FIG. 4E. The base 460 is a portion of the neck seal 428 that attaches, mates, interfaces, squeezes, grabs, or otherwise couples with the neck ring 418. In some embodiments, less than all of the base 460 couples with the neck ring 418. In some embodiments, most of the base 460 couples with the neck ring 418. In some embodiments, the entirety of the base 460 couples with the neck ring 418. In some embodiments, more than just the base 460 of the neck seal 428 couples with the neck ring 418. For example, the base 460 and part of the upper 462 may couple with the neck ring 418.

As shown, the base 460 may be thicker than the upper 462. The base 460 may further include parts, projections or elements that are thicker than the upper 462. The upper 462 may further have variable thickness along its length, as is discussed in further detail herein, for example with respect to FIG. 5C.

As shown in FIG. 4E, the neck seal 428 may include a first sealing element 466 and a second sealing element 464 coupled with the base 460. The sealing elements 466, 464 can be configured to seal with the neck ring 418. The sealing elements 464, 466 may comprise inward projections such that they project inward toward the center of the tubular neck seal 428. The sealing elements 464, 466 may form an annular structure that extends at least partially around a corresponding perimeter of the base 460. In some embodiments, the sealing elements 464, 466 run along the entire perimeter of the base 460 of the neck seal 428. Thus, the sealing elements 464, 466 may form a complete, circumferential structure on a surface of the base 460 of the neck seal 428. In some embodiments, the sealing elements 464, 466 run along the entire inner perimeter of the base 460 and form a complete, circumferential structure on an inner surface or surfaces of the base 460.

Embodiments of the neck seals herein, such as the neck seal 28 or 428 for example, can include two or more sealing elements, not just to provide increased sealing protection, but to prevent disengagement of a neck seal from a corresponding neck ring. For example, a neck seal with a single sealing element, and in particular, a single sealing element with a round cross-sectional area, has a tendency to disengage with the corresponding neck ring. For example, the radial forces inherent to the engagement interface between the neck seal and neck ring may cause a single sealing element neck seal to roll off the end of the corresponding neck ring. Two or more sealing elements, and various additional structural configurations thereof, can provide additional transverse and longitudinal stability that can prevent such failure in single sealing element designs.

The sealing elements 464, 466 can be positioned relative to each other in different ways. For example, sealing elements 464, 466 can be approximately longitudinally spaced with respect to each other, as shown, or transversely (e.g., radially) spaced with respect to each other, or both. Sealing elements 464, 466 can be approximately longitudinally aligned with each other, as shown, or radially aligned, or aligned with each other along an axis angled relative to neck seal 428. A transverse or longitudinal gap can be formed between the sealing elements 464, 466.

The sealing elements 464, 466 may have a variety of cross-sectional shapes. In some embodiments, at least one of the sealing elements 464, 466 have a non-circular shaped cross-section. At least one, or as shown, both, the sealing elements 464, 466 can have a generally rectangular shaped cross-section. In some embodiments, the sealing elements 464, 466 can have a generally square shaped cross-section. Embodiments of neck seals wherein at least one of the sealing elements 464, 466 includes such non-circular shaped cross-sections, can prevent the neck seal 428 from disengaging with the neck ring 418. For example, a neck seal with a non-circular shaped cross-section may prevent the neck seal from rolling off, and thus disengaging from, the end of the neck ring, as described further below.

While the sealing elements 464, 466 are shown having three sides, they may have any number of sides. For example, the sealing elements 464, 466 may have one, two, three, four or more sides. Further, the various sides of the sealing elements 464, 466 may be straight, curved, or combinations thereof. In some embodiments, the sealing elements 464, 466 have three generally straight sides. In some embodiments, at least one of the sealing elements 464, 466 includes at least one substantially straight side, with a corresponding substantially flat surface, to prevent the neck seal 428 from disengaging with the neck ring 418. For example, a neck seal with two sealing elements, at least one of which has a substantially straight side and a corresponding flat surface, may prevent the neck seal from rolling off, and thus disengaging from, the end of the neck ring, as described further below.

The shapes, positioning, and other configurations of the sealing elements 464, 466 are described herein, unless stated otherwise, when the neck seal 428 is in a free state. It will be understood that some amount of deformation of the neck seal 428 may occur when the neck seal 428 is engaged with (e.g., sealed against) the neck ring 418, without departing from the scope of the described shapes, positioning, etc. of the sealing elements 464, 466 or other features of the neck seal 428. For example, the sealing elements 464, 466 may be sized slightly larger than the corresponding grooves in the neck ring 418, to allow for compression during engagement of the neck seal 428 and neck ring 418. However, these components may all be sized such that the compression is approximately uniform, to reduce deviation of the shape of these components during said engagement. Further, the sealing elements 464, 466 may have different shapes or orientations with respect to each other. In some embodiments, the second sealing element 464 has a different shape, orientation, size, configuration, etc. as compared with the first sealing element 466, in either the free state and/or when stretched, for example, when attached to the neck ring 418.

As shown, the first sealing element 466 may include a first lower surface 468. The first lower surface 468 may contact the neck ring 418. In some embodiments, the first lower surface 468 interfaces with the neck ring 418 in a substantially horizontal configuration. In some embodiments, the first lower surface 468 rests on top of the neck ring 418.

In some embodiments, the first lower surface 468 conforms to the contour of the surface of the neck ring 418 at the interface where the first lower surface 468 contacts the neck ring 418. Thus, the first lower surface 468 may be angled or off-horizontal before coupling with the neck ring 418, i.e. in its free state, and horizontal or substantially horizontal after coupling with the neck ring 418. The first lower surface 468 may further take other configurations or orientations to conform with the surface of the neck ring 418 that the first lower surface 468 contacts. For example, while the first lower surface 468 is shown as flat in FIG. 4E, the first lower surface 468 may have shapes or contours other than flat, such as curvilinear. The first lower surface 448 may have a shape that complements the shape or contour of the surface of the neck ring 418 with which the first lower surface 468 contacts.

In some embodiments, the first lower surface 468 exerts a force at the interface with the neck ring 418. For instance, the first lower surface 468 as shown may exert a downward force at the interface with the neck ring 418. In some embodiments, a seal is created along the interface between the first lower surface 468 and the neck ring 418, such that little or no gas may flow between the base 460 and the neck ring 418 at the interface between the neck ring 418 and the first lower surface 468.

As shown, the first sealing element 466 may further include a first inner surface 470 that is coupled to the first lower surface 468. The first inner surface 470 may contact the neck ring 418. In some embodiments, the first inner surface 470 interfaces with the neck ring 418 in a substantially vertical configuration. In some embodiments, the first inner surface 470 is adjacent to but not contacting the neck ring 418.

In some embodiments, the first inner surface 470 contacts the neck ring 418 and exerts an inward force at the interface with the neck ring 418. In some embodiments, a seal is created along the interface between the first inner surface 470 and the neck ring 418, such that little or no gas may flow between the base 460 and the neck ring 418 at the interface between the neck ring 418 and the first inner surface 470.

In some embodiments, the first inner surface 470 conforms to the contour of the surface of the neck ring 418 at the interface where the first inner surface 470 contacts the neck ring 418. Thus, the first inner surface 470 may be angled or off-vertical before coupling with the neck ring 418 and vertical or substantially vertical after coupling with the neck ring 418. The first inner surface 470 may further take other configurations or orientations to conform with the surface of the neck ring 418 that the first inner surface 470 contacts. For example, while the first inner surface 470 is shown as flat in FIG. 4E, the first inner surface 470 may have shapes or contours other than flat, such as curvilinear.

As shown, the first sealing element 466 may include a first upper surface 472 that is coupled with the first inner surface 470. The first upper surface 472 may contact the neck ring 418. In some embodiments, the first upper surface 472 interfaces with the neck ring 418 in a substantially horizontal configuration. In some embodiments, the first upper surface 472 rests underneath the neck ring 418.

In some embodiments, the first upper surface 472 exerts an upward force at the interface with the neck ring 418. In some embodiments, a seal is created along the interface between the first upper surface 472 and the neck ring 418, such that little or no gas may flow between the base 460 and the neck ring 18 at the interface between the neck ring 418 and the first upper surface 472.

In some embodiments, the first upper surface 472 conforms to the contour of the surface of the neck ring 418 at the interface where the first upper surface 472 contacts the neck ring 418. Thus, the first upper surface 472 may be angled or off-horizontal before coupling with the neck ring 418 and horizontal or substantially horizontal after coupling with the neck ring 418. The first upper surface 472 may further take other configurations or orientations to conform with the surface of the neck ring 418 that the first upper surface 472 contacts. For example, while the first upper surface 472 is shown as flat in FIG. 4E, the first upper surface 472 may have shapes or contours other than flat, such as curvilinear.

As shown, the base 460 may include a first outer surface 474 that is coupled with the first upper surface 472. The first outer surface 474 may have features and functionalities that are similar to the first inner surface 470, as discussed in further detail herein. For example, the first outer surface 474 may be adjacent to or contact the neck ring 418, the first outer surface 474 may be vertical or substantially vertical when configured with the neck ring 418, the first outer surface 474 may be angled or off-vertical in its free or natural state, i.e. before coupling with the neck ring 418, etc.

The first sealing element 466 may therefore include the first lower surface 468, the first inner surface 470, the first upper surface 472 and the first outer surface 474. In some embodiments, the first sealing element 466 may include only the first lower surface 468, the first inner surface 470 and the first upper surface 472, while the first outer surface 474 may be a transitional structure between the first sealing element 466 and the second sealing element 464. Thus, the discussion of certain features of the neck seal 428 in the context of one sealing element or the other is not meant to limit those features as belonging to either element. For example, in some embodiments, the first outer surface 474 is part of the second sealing element 464.

The base 460 may further include the second sealing element 464. In some embodiments, the second sealing element 464 is coupled to the first sealing element 466. In some embodiments, the second sealing element 464 and the first sealing element 466 are each coupled to a transitional structure therebetween, such as the first outer surface 474.

In some embodiments, the second sealing element 464 includes a second lower surface 476 coupled to the first outer surface 474. The second lower surface 476 may include similar features and functionalities as the first lower surface 468, as discussed in further detail herein. For example, the second lower surface 476 may contact the neck ring 418, the second lower surface 476 may be horizontal or substantially horizontal when configured with the neck ring 418, the second lower surface 476 may be angled or off-horizontal in its free state, i.e. when it is not coupled with the neck ring 418, the second lower surface 476 may prevent or mitigate the passage of gas flow along the interface between the second lower surface 476 and the neck ring 418, etc.

As shown, the second sealing element 464 may include a second inner surface 478 that is coupled with the second lower surface 476. The second inner surface 478 of the second sealing element 464 may include features and functionalities that are similar to the first inner surface 470 of the first sealing element 466, as discussed in further detail herein. For example, the second inner surface 478 may be vertical or substantially vertical when configured with the neck ring 418, the second inner surface 478 may be angled or off-vertical in its free state, i.e. before coupling with the neck ring 418, the second inner surface 478 may be adjacent to or contacting the neck ring 418, the second inner surface 478 may prevent or mitigate the flow of gas along the interface where the second inner surface 478 contacts or is adjacent to the neck ring 418, etc.

As shown, the second sealing element 464 may further include a second upper surface 480 that is coupled to the second inner surface 478. The second upper surface 480 may include features and functionalities that are similar to the first upper surface 472, as discussed in further detail herein. For example, the second upper surface 480 may contact the neck ring 418 along a horizontal or substantially horizontal interface, the second upper surface 480 may be angled or off-horizontal in its free state, i.e. before coupling with the neck ring 418, the second upper surface 480 may prevent or mitigate the flow of gas along the interface where the second upper surface 480 contacts the neck ring 418, etc.

The various surfaces of the sealing elements 464, 466 may be coupled along tubular edges between the surfaces. For instance, as shown in FIG. 4E, the second inner surface 478 may be coupled with the second upper surface 480 by the edge 479. As shown, the edge 479 may be rounded. In some embodiments, the outer corner may be a radius, circular, elliptical, oval, or other rounded shape. The edge 479 may further be a sharp angle. In some embodiments, the edge 479 is a sharp corner that is roughly ninety degrees.

The edge 479 may further be between various other surfaces as well. In some embodiments, other surfaces have similar features and functionalities as the edge 479, including but not limited to the surfaces between the first lower surface 468 and the first inner surface 470, between the first inner surface 470 and the first upper surface 472, between the second lower surface 476 and the second inner surface 478, and between the second inner surface 478 and the second upper surface 480.

As shown, the base 460 may include a second outer surface 482 that is coupled with the second upper surface 480. The second outer surface 482 may have features and functionalities that are similar to the first outer surface 474, as discussed in further detail herein. For example, the second outer surface 482 may be adjacent to or contact the neck ring 418, the second outer surface 482 may be vertical or substantially vertical when configured with the neck ring 418, the second outer surface 482 may be angled or off-vertical in its natural state, i.e. before coupling with the neck ring 418, etc.

Further, the second outer surface 482 may be a shoulder comprising a relatively thicker portion of the neck seal 428. For instance, as shown in FIG. 4E, the second outer surface 482 is at a thicker portion of the neck seal 428 than the upper 462. The thicker portion at the second outer surface 482 provides a number of benefits. For instance, the thicker portion at the second outer surface 482 may provide robustness to the neck seal 428, allow for higher forces on the base 460 to ensure a tighter seal, mitigate the effects of wear and tear, etc.

The second sealing element 464 may therefore include the second lower surface 476, the second inner surface 478, and the second upper surface 480. In some embodiments, the second sealing element 464 includes the second outer surface 482. In some embodiments, the second sealing element 464 includes the first outer surface 474.

The various surfaces of the sealing elements 464, 466 may be coupled along tubular corners between the surfaces. For instance, as shown in FIG. 4E, the second upper surface 480 may be coupled with the second outer surface 482 by a corner 481. The corner 481 may have similar features and functionalities as the edge 479. As shown, the corner 481 may be rounded. In some embodiments, the corner 481 may be a radius, circular, elliptical, oval, or other rounded shape. The corner 481 may further be a sharp angle. In some embodiments, the corner 481 is a sharp corner that is roughly ninety degrees.

The corner 481 may further be between various other surfaces as well. In some embodiments, other corner surfaces have similar features and functionalities as the corner 481, including but not limited to the surfaces between the first upper surface 472 and the first outer surface 474 and between the first outer surface 474 and the second lower surface 476.

The neck seal 428 may prevent or mitigate the flow of gas across the interface between the neck seal 428 and the neck ring 418. In some embodiments, the base 460 prevents or mitigates the flow of gas across the interface between the base 460 and the neck ring 418. In some embodiments, the sealing elements 464, 466 prevent or mitigate the flow of gas across the interface between the sealing elements 464, 466 and the neck ring 418.

The sealing elements 464, 466 may further assist with mechanically attaching the neck seal 428 to the neck ring 418. In some embodiments, the sealing elements 464, 466 elastically expand and contract to impart an inward force on the neck ring 418. For instance, the sealing elements 464, 466 may expand to fit around the neck ring 418 and then contract onto the neck ring 418 to provide a snug fit.

The sealing elements may further assist with both attachment and prevention of gas flow. In some embodiments, both sealing elements 464, 466 facilitate with mechanically attaching to the neck ring 418 as well as with preventing the flow of gas across the interface between the sealing elements 464, 466 and the neck ring 418. In some embodiments, one of the sealing elements primarily serves to assist with attachment while the other of the sealing elements primarily serves to prevent gas flow. For instance, the first sealing element 466 may primarily assist with mechanical attachment and retention while the second sealing element 464 may primarily assist with preventing gas flow, or vice versa. In some embodiments, the second sealing element 464 prevents substantially all gas flow such that the first sealing element 466 does not contact any gas flow originating from inside the hood assembly 410, for example, such that first sealing element 466 is redundant, to provide sealing in the event of failure of second sealing element 464.

Embodiments of the at least two sealing elements described herein can also provide improved engagement between the neck seal and neck ring. For example, a neck seal with a single sealing element, particularly one with a round cross-sectional seal shape, such as that shown in FIG. 3, may be susceptible to failure, for example, when the single sealing element rolls off the end of the neck seal. Embodiments of the neck seals herein, which include at least two sealing elements, provide both transverse and longitudinal stability at the sealing interface, as well as additional surface area contact, relative to a single seal design, for improved sealing function at the interface between the neck seal and the neck ring. One or more of the various features described above, such as the orientation of the dual-sealing elements with respect to each other, the quantity, positioning, orientation, and shape of the sealing elements, and their features (such as their surfaces), as well as their interactions with corresponding features on the base and the neck ring, can both improve the sealing through reduced leakage, and improve engagement between the neck seal and the neck ring, and thus reduce neck seal failure.

It will be understood that the neck rings described herein, such as neck ring 418 shown in FIG. 4B, can include structural features that are similar or complementary to the neck seals and sealing elements described herein. For example, the neck rings can include two or more corresponding annular grooves configured to approximately conform to, and thus engage with, the sealing elements 464, 466, as described above. The grooves, and/or other features of the neck rings can be shaped and/or positioned similarly as the sealing elements 464, 466. For example, as shown in FIG. 4E, the neck ring 418 can include a neck ring base 422 with a neck ring sidewall 419 extending therefrom. The sidewall 419 can extend from the neck ring base 422 at an angle, for example, approximately orthogonally, as shown, or at other angles. The sidewall 419 can extend from the neck ring base 422, for example, approximately horizontally and/or radially outwardly, as shown, or at other orientations. The neck ring 418 can include at least two neck ring protrusions 421, 423, which can extend from the neck ring base 422 at an angle sufficient to form annular grooves 427, 429 configured to receive the sealing elements 464, 466 of the neck ring 418. The neck ring 418 can include various surfaces, for example, on the upper surface of sidewall 419, within the annular grooves 427, 429, and/or on the neck ring protrusions 421, 423 that conform with and/or engage with the aforementioned corresponding surfaces on the neck seal 428.

Figure 5A:
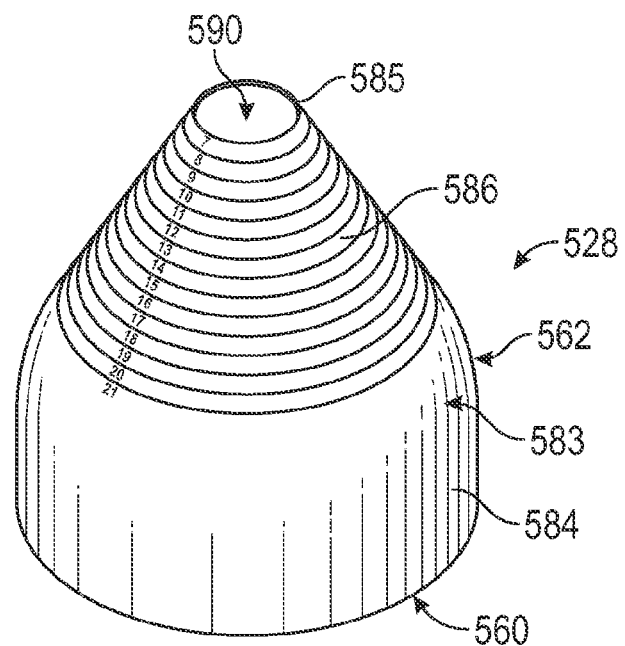
FIG. 5A is a perspective view of the neck seal of FIGS. 4A-4E.
Figure 5B:
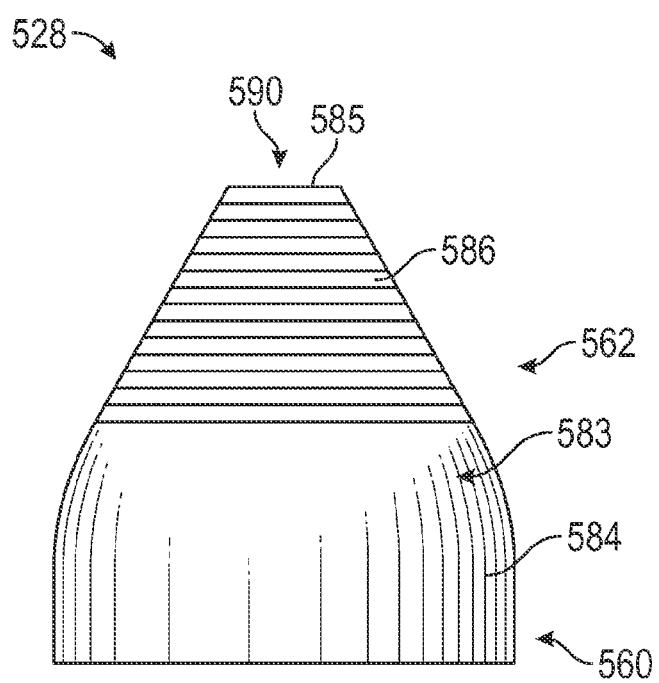
FIG. 5B is a side view of the neck seal of FIGS. 4A-4E.

FIGS. 5A and 5B are perspective and side views, respectively, of an embodiment of a neck seal 528 having a sidewall 583 of variable thickness. The neck seal 528 may have the same or similar features as other neck seals described herein, for example the neck seal 428, and vice versa.

As shown in FIGS. 5A and 5B, the neck seal 528 may include an upper 562 and a base 560. The upper 562 may be an upper portion of the neck seal 528 that is coupled with the base 560. The upper 562 and base 560 may be a monolithic part or may be separate parts that are connected together. As shown, the neck seal 528 may include a tubular sidewall 583. The tubular sidewall may include portions of the upper 562 and/or the base 560. The neck seal 528 may have a top 585. The top 585 may be an upper part or upper edge of the sidewall 583. The top 585 may form the opening 590 at the top of the neck seal 528 as oriented. The sidewall 583 may include a first straight section 584 and/or a second straight section 586. The first straight section 584 may be coupled with the second straight section 586.

Figure 5C:
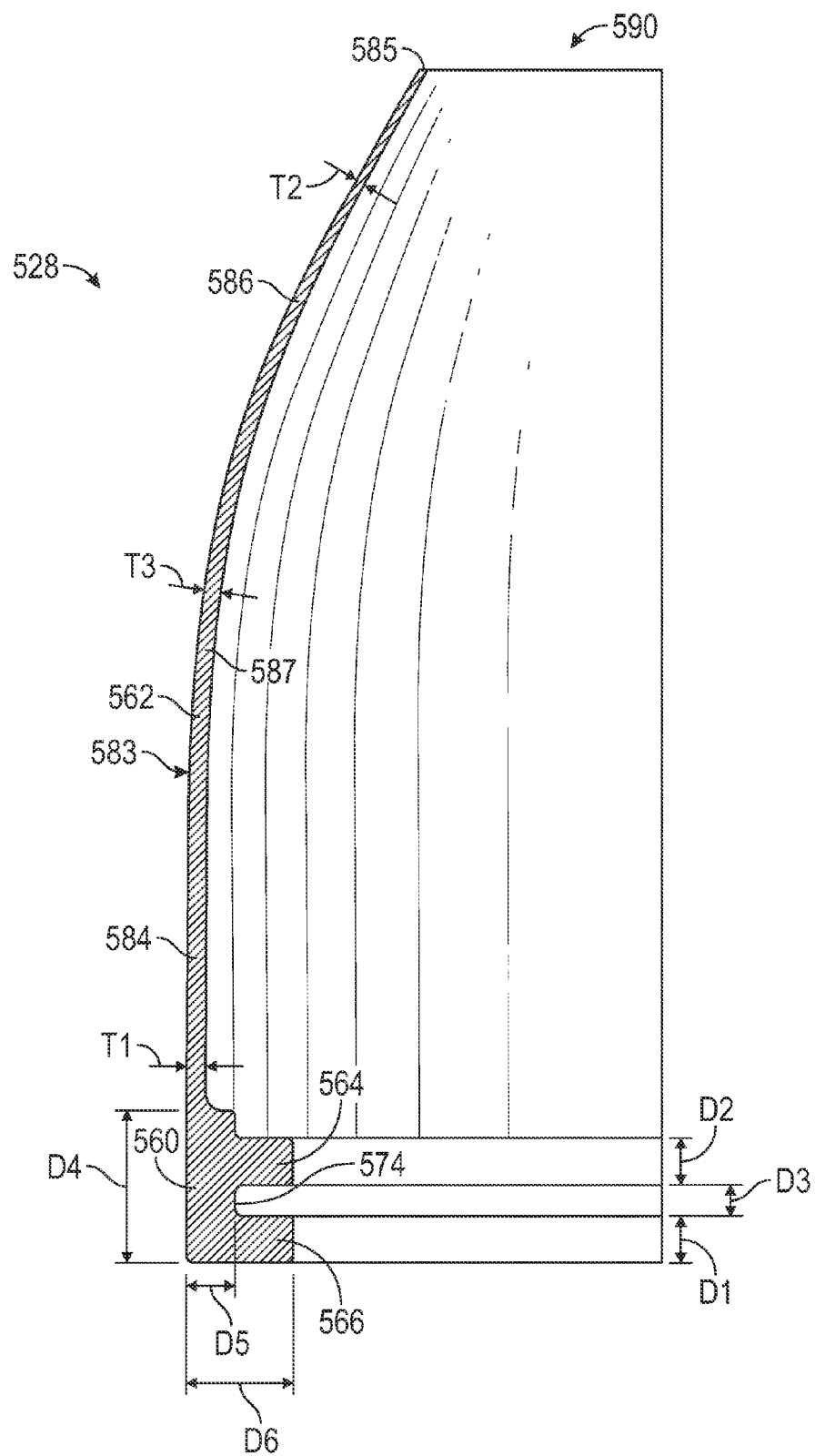
FIG. 5C is a partial cross-section view of the neck seal of FIGS. 4A-4E.

FIG. 5C is a partial cross-section view of the neck seal 528. As shown, the neck seal 528 may include the base 560 with the upper 562. The upper 562 may extend upward along a generally longitudinal direction from the base 560. The base 560 may include sealing elements 564, 566. The base 560 may have the same or similar features as other bases described herein, for example the base 460, and vice versa. The sealing elements 564, 566 may have the same or similar features as other sealing elements described herein, for example the sealing elements 464, 466, and vice versa.

As further shown in FIG. 5C, the upper 562 may include the sidewall 583. The sidewall 583 may extend from the base 560 to the top 585 forming the opening 590 of the neck seal 528. The top 585 may be an end or edge to the sidewall 583. Further, the top 585 may be in various locations and heights, for example, depending on whether the neck seal 528 has been trimmed to fit a user.

The thickness of the sidewall 583 can be different at various points along its length. For example, a first thickness, such as thickness T1 discussed below, of the sidewall 583 adjacent to the base 560 can be greater than a second thickness, such as thickness T2 discussed below, of the sidewall adjacent to the top 585. Such an embodiment can provide greater flexibility and comfort around a user's neck, while providing increased strength and sealing between the neck seal and the ring. The thickness of the sidewall 583 can vary (uniformly or non-uniformly) along its length. For example, sidewall 583 can comprise a plurality of intermediate thicknesses that decrease substantially uniformly along at least a portion of the sidewall from the first thickness, such as thickness T1, to the second thickness, such as thickness T2.

The sidewall 583 may include sections of various shapes, sizes, contours, etc. As shown, the sidewall 583 may include the first straight section 584 extending from the base 560. The first straight section 584 may be substantially straight. In some embodiments, the first straight section 584 is generally straight and vertical, as oriented in the figure. In some embodiments, the first straight section 584 is generally straight and angled or off-vertical with respect to base 560.

The first straight section 584 may further have various thicknesses. As shown in FIG. 5C, the thickness of the first straight section 584 at a particular location (such as adjacent or proximate to the base 560) is designated as first thickness T1. While T1 is indicated at a particular position along the first straight section 584, it may be at any position along the first straight section 584. In some embodiments, T1 is substantially uniform or constant along the first straight section 584. In some embodiments, T1 may be between approximately 0.015 inches and 0.100 inches, inclusive. "Inclusive" is used herein in its usual and ordinary sense to include the values on the endpoints of a given range. Thus, the possible values of T1 in some embodiments includes 0.015 inches and 0.100 inches. In some embodiments, T1 may be about 0.060 inches. In some embodiments, the entire first straight section 584 is about 0.060 inches thick.

As shown, the sidewall 583 may further include a second straight section 586. The second straight section 586 may have similar features and functionalities as the first straight section 584. The second straight section 586 may be substantially straight. In some embodiments, the second straight section 586 is generally straight, and angled with respect to first straight section 584, as oriented in the figure. In some embodiments, the second straight section 586 is generally straight and vertical.

The second straight section 586 may further have various thicknesses. As shown in FIG. 5C, the thickness of the second straight section 586 at a particular location (such as adjacent or proximate to top 585) is designated as a second thickness T2. While the second thickness T2 is indicated at a particular position along the second straight section 586, it may be at any position along the second straight section 586. In some embodiments, the second thickness T2 is substantially uniform or constant along the second straight section 586. In some embodiments, the second thickness T2 may be between approximately 0.010 inches and 0.050 inches, inclusive. In some embodiments, the second thickness T2 may be about 0.040 inches. In some embodiments, the entire second straight section 586 is about 0.040 inches thick.

The values for the first thickness T1 and the second thickness T2 may be dependent on each other. In some embodiments, the first thickness T1 may be a particular percentage larger than the second thickness T2. For instance, the first thickness T1 may be twenty-five to three hundred percent (25-300%) larger than the second thickness T2. In some embodiments, the first thickness T1 may be fifty percent (50%) larger than the second thickness T2.

As shown, the sidewall 583 may further include a curved section 587. In some embodiments, the curved section 587 extends from the first straight section 584 to the second straight section 586. The curved section 587 may have any number of different types of curvatures. In some embodiments, the curved section 587 is a radius. The curved section 587 may further be an elliptical curve, an oval curve, a non-uniform curve, and/or combinations thereof. In some embodiments, the curved section 587 comprises an outwardly-convex shape. In some embodiments, the curved section 587 is a combination of curved and straight subsections. For example, the curved section 587 may include some partially curved sub-sections and/or partially straight sub-sections. Generally, the curved section 587 can comprise a transitional section of any suitable shape that transitions the neck seal 528 from the relatively larger opening formed by base 560, to the relatively smaller opening formed by the top 585.

The curved section 587 may further have various thicknesses. As shown in FIG. 5C, the thickness of the curved section 587 at a particular location is designated as an intermediate thickness T3. While the intermediate thickness T3 is indicated at a particular position along the curved section 587, it may be at any position along the curved section 587. The intermediate thickness T3 may further have various values. In some embodiments, the intermediate thickness T3 is substantially uniform or constant along the curved section 587. In some embodiments, the intermediate thickness T3 falls within the ranges described with respect to thicknesses T1 and T2. For example, T3 may be between approximately 0.010 inches and 0.100 inches, inclusive. In some embodiments, the intermediate thickness T3 may be about 0.060 inches. In some embodiments, the intermediate thickness T3 may be about 0.040 inches.

The intermediate thickness T3 of the curved section 587 may be variable along the curved section 587. In some embodiments, the intermediate thickness T3 decreases from a relatively larger thickness near the first straight section 584 to a relatively smaller thickness on the opposite end of the curved section 587 near the second straight section 586. For example, the intermediate thickness T3 of the curved section 587 near the first straight section 584 may be between approximately 0.015 inches and 0.100 inches, inclusive, while the intermediate thickness T3 of the curved section 587 near the second straight section 586 may be between approximately 0.010 inches and 0.050 inches, inclusive. In some embodiments, the intermediate thickness T3 of the curved section 587 near the first straight section 584 is 0.060 inches. In some embodiments, the intermediate thickness 5T3 of the curved section 587 near the second straight section 586 is 0.040 inches. Thus, in some embodiments of the neck seal 528, the first straight section 584 may have a uniform first thickness T1 equal to about 0.060 inches, the second straight section 586 may have a uniform second thickness T2 equal to about 0.040 inches, and the curved section 587 may have a variable intermediate thickness T3 that is equal to about 0.060 inches near the first straight section 584 and equal to about 0.040 inches near the second straight section 586. In some embodiments, the intermediate thickness T3 of the curved section 587 decreases substantially uniformly from about 0.060 inches near the first straight section 584 to about 0.040 inches near the second straight section 586. By "decreases substantially uniformly" it is meant that the value of the intermediate thickness T3 continually decreases and does not significantly increase (other than minor variances due to tolerancing, for example within the manufacturing equipment) from the first straight section 584 to the second straight section 586. In some embodiments, the intermediate thickness T3 decreases along the curved section 587 at a linear rate. For example, the thickness T3 may decrease by a set amount per dimensional unit, e.g. the thickness T3 may decrease by 0.010 inch per 1 inch along the sidewall. In some embodiments, the intermediate thickness T3 decreases along the curved section 587 at a rate other than linear, e.g. parabolic, exponential, random, etc.

The neck seal 528 and associated parts thereof, such as the base 560 and the upper 562, may comprise various materials having various properties. In some embodiments, the neck seal 528 is made of a stretchable material. In some embodiments, the neck seal 528 is made of an elastomeric material. By "elastomeric" it is meant the material is elastic, such as a polymer or other material with a Young's modulus low enough to allow it to stretch, seal and otherwise provide the attachment and/or sealing functions described herein. In some embodiments, the neck seal 528 or portions thereof may be made of silicone. In some embodiments, the neck seal 528 or portions thereof may be made of medical grade silicone. In some embodiments, the neck seal 528 or portions thereof may be made of medical grade Class VI silicone. In some embodiments, the neck seal 528 or portions thereof may be made of medical grade 25D silicone. In some embodiments, the neck seal 528 comprises a material with a Shore Hardness A Durometer between approximately 10 and 30, inclusive. In some embodiments, the neck seal 528 comprises a material with a Shore Hardness A Durometer between approximately 520 and 525, inclusive. Therefore, in some embodiments, the neck seal 528 or portions thereof may be made of medical grade Class VI silicone with a Shore Hardness A Durometer between approximately 520 and 525, inclusive. Use of one or more of these materials can provide a neck seal with a thicker wall, while still being sufficiently stretchable to provide sufficient sealing and comfort to the user.

Further, the neck seal 528 and associated parts thereof, such as the base 560, the sealing elements 564, 566, and the upper 562, may be one or more parts. In some embodiments, the entire neck seal 528, including the base 560, the sealing elements 564, 566, and the upper 562, is a single, unitary or otherwise monolithic part. For instance, the base 560, sealing elements 564, 566, and the upper 562 may be constructed by injection molding to form a unitary, molded construction.

In some embodiments, the neck seal 528 may be manufactured using an injection molding process. This process may use a precision molding tool that allows for more precise geometric dimensioning and tolerancing of the neck seal 528. In some embodiments, the tool includes a mold with a space or cavity into which fluid elastomeric material is injected. The space created by the mold may determine the final shape of the neck seal 528. The fluid elastomeric material may then harden in the desired shape and form a solid neck seal 528 that can be removed from the mold. In some embodiments, a precision mold is used having a space with a cross-sectional shape approximately in the shape of the cross-section of the neck seal as shown in FIG. 5C. Injection molding thus allows for better control of the thicknesses of various areas of the neck seal 528, such as the base 560, the sealing elements 564, 566, the first straight section 584, the curved section 587, and/or the second straight section 586. Injection molding further allows for production of complex shapes to the sealing elements 564, 566, such as square, round, etc. Injection molding further allows for producing a latex-free neck seal 528, such as a 25D medical grade silicone neck seal 528.

Further shown in FIG. 5C are various dimensions of various portions of the neck seal 428. As shown, the sealing element 566 may have a thickness D1. In some embodiments, D1 may be 0.150 inches. The sealing element 564 may have a thickness D2. In some embodiments, D2 may be 0.150 inches. Sealing elements 564, 566 may be spaced apart a distance D3. In some embodiments, D3 may be 0.094 inches. The base 560 may have an overall length of D4. In some embodiments, D4 may be 0.488 inches. A first inner surface 574, which may be similar to the inner surface 470 described above, may have a length D5 as indicated. In some embodiments, D5 may be 0.150 inches. The sealing elements 564, 566 may have a length of D6 as indicated. In some embodiments, D6 may be 0.337 inches. In some embodiments, corners of the sealing elements 564, 566 may have a radius. In some embodiments, the radius may be 0.030 inches. These values for the various dimensions are merely examples. Other embodiments may have values for these dimensions that are approximately the same as those explicitly given. Other embodiments may have values for these dimensions that are different.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

The foregoing description details certain embodiments of the invention disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several devices and systems of the present invention. This invention is susceptible to modifications in the methods, devices and systems. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the following claims.

What is claimed is:

1. A neck seal for a gas treatment hood, the neck seal comprising:
   a tubular stretchable base defining an axis and comprising at least first and second sealing elements integral with the base and extending substantially radially inward toward the axis from an inner perimeter of the base, the first and second sealing elements configured to seal with corresponding grooves of a tubular neck ring; and a tubular stretchable upper integral with the base, the upper comprising a sidewall extending upward from the base to a top of the upper, the top forming an opening configured to fit around a user's neck, wherein a first thickness of the sidewall at a first location of the sidewall that is adjacent to the base is greater than a second thickness of the sidewall at a second location of the sidewall that is adjacent to the top.

2. The neck seal of claim 1, the sidewall further comprising:
   a plurality of intermediate thicknesses that decrease substantially uniformly along at least a portion of the sidewall from the first thickness to the second thickness.

3. The neck seal of claim 1, the sidewall further comprising:
   a first substantially straight section coupled with the base and having a first straight section thickness equal to the first thickness;
   a curved section having a lower end and an upper end, wherein the lower end is coupled with the first straight section; and
   a second substantially straight section coupled with the upper end of the curved section and having a second straight section thickness equal to the second thickness, and
   wherein the curved section comprises a plurality of intermediate thicknesses that decrease substantially uniformly, from a first curved section thickness at the lower end that is equal to the first thickness, to a second curved section thickness at the upper end that is equal to the second thickness.

4. The neck seal of claim 1, wherein the first thickness is about 25% to 300% thicker than the second thickness.

5. The neck seal of claim 1, wherein the neck seal comprises a material with a Shore Hardness A Durometer between approximately 10 and 30, inclusive.

6. The neck seal of claim 1, wherein the neck seal is silicone.

7. The neck seal of claim 1, the base further comprising:
   at least two sealing elements configured to couple with the tubular neck ring.

8. A gas treatment hood assembly comprising the neck seal of claim 1, a hood and the neck ring.

9. A neck seal for a gas treatment hood, the neck seal comprising:
   a tubular stretchable upper comprising a top with an opening configured to fit around a user's neck;
   a tubular stretchable base coupled with the upper and defining an axis, wherein the upper extends upwardly from the base; and
   at least first and second sealing elements integral with the base and extending radially inward toward the axis along an inner perimeter of the base, the first and second sealing elements configured to seal with corresponding grooves of a tubular neck ring.

10. The neck seal of claim 9, wherein at least one of the first and second sealing elements has a substantially rectangular cross-section.

11. The neck seal of claim 9, wherein the first and second sealing elements each comprise:
    a tubular top surface, a tubular inner surface and a tubular bottom surface,
    wherein, when coupled with the tubular neck ring, the top and bottom surfaces are substantially horizontal and the inner surfaces are substantially vertical.

12. The neck seal of claim 9, wherein the neck seal has a Shore Hardness A Durometer between approximately 10 and 30, inclusive.

13. The neck seal of claim 9, wherein the neck seal is silicone.

14. The neck seal of claim 9, wherein the tubular elastomeric upper further comprises:
    a sidewall extending upward from the base to the top,
    wherein a first thickness of the sidewall adjacent to the base is greater than a second thickness of the sidewall adjacent to the top.

15. The neck seal of claim 14, the sidewall further comprising:
    a plurality of intermediate thicknesses that decrease substantially uniformly along the sidewall from the first thickness to the second thickness.

16. The neck seal of claim 14, wherein the upper further comprises:
    a first substantially straight section coupled with the base and having a first straight section thickness equal to the first thickness;
    a curved section having a lower end and an upper end, wherein the lower end is coupled with the first straight section; and
    a second substantially straight section coupled with the upper end of the curved section and having a second straight section thickness equal to the second thickness, and
    wherein the curved section comprises a plurality of intermediate thicknesses that decrease substantially uniformly, from a first curved section thickness at the lower end equal to the second thickness, to a second curved section thickness at the upper end equal to the second thickness.

17. A gas treatment hood assembly comprising the neck seal of claim 14 and the neck ring, wherein the neck ring comprises at least two annular grooves, each groove configured to receive a corresponding one of the first and second sealing elements.

18. A neck ring for a gas treatment hood, the neck ring comprising:
    a tubular base defining an axis and forming an opening configured to fit around a user's neck;
    a sidewall extending from the base radially outward away from the axis;
    at least two protrusions integral with and extending from the base radially outward away from the axis, the two protrusions forming at least two annular grooves in the base, the annular grooves each configured to receive a corresponding sealing element of a tubular neck seal that extends radially inward toward the axis when received by a corresponding groove of the at least two annular grooves.

19. The neck ring of claim 18, wherein the at least two annular grooves comprise a first annular groove formed between a first of the at least two protrusions and a second of the at least two protrusions, and a second annular groove formed between a second of the at least two protrusions and the sidewall.

20. The neck ring of claim 18, wherein at least one of the at least two annular grooves has a substantially rectangular cross-section.

* * * * *

UNITED STATES PATENT AND TRADEMARK OFFICE
CERTIFICATE OF CORRECTION

PATENT NO. : 9,931,482 B2
APPLICATION NO. : 14/681935
DATED : April 3, 2018
INVENTOR(S) : Scott Craig Ritchie et al.

It is certified that error appears in the above-identified patent and that said Letters Patent is hereby corrected as shown below:

In the Specification

In Column 19 at Line 26, Change "5T3" to --T3--.

Signed and Sealed this
Tenth Day of July, 2018

Andrei Iancu
*Director of the United States Patent and Trademark Office*